(12) United States Patent
Hennings et al.

(10) Patent No.: US 9,144,463 B2
(45) Date of Patent: *Sep. 29, 2015

(54) TREATMENT OF CELLULITE AND ADIPOSE TISSUE WITH MID-INFRARED RADIATION

(71) Applicants: David R. Hennings, Roseville, CA (US); Mitchel P. Goldman, Roseville, CA (US)

(72) Inventors: David R. Hennings, Roseville, CA (US); Mitchel P. Goldman, Roseville, CA (US)

(73) Assignee: COOL TOUCH INCORPORATED, Roseville, CA (US)

( * ) Notice: Subject to any disclaimer, the term of this patent is extended or adjusted under 35 U.S.C. 154(b) by 58 days.

This patent is subject to a terminal disclaimer.

(21) Appl. No.: 13/743,068

(22) Filed: Jan. 16, 2013

(65) Prior Publication Data

US 2013/0131658 A1  May 23, 2013

Related U.S. Application Data

(60) Division of application No. 12/101,095, filed on Apr. 10, 2008, now Pat. No. 8,357,146, which is a continuation-in-part of application No. 11/847,153, filed on Aug. 29, 2007, now Pat. No. 8,256,429, which is a continuation-in-part of application No. 11/675,028, filed on Feb. 14, 2007, now Pat. No. 8,127,771, which is a continuation-in-part of application No. 11/131,577, filed on May 18, 2005, now Pat. No. 7,217,265.

(51) Int. Cl.
| | |
|---|---|
| *A61B 19/00* | (2006.01) |
| *A61B 18/28* | (2006.01) |
| *A61B 18/22* | (2006.01) |
| *A61B 18/20* | (2006.01) |
| *A61N 5/06* | (2006.01) |

(52) U.S. Cl.
CPC .............. *A61B 18/28* (2013.01); *A61B 18/22* (2013.01); *A61B 2018/2005* (2013.01); *A61N 2005/0659* (2013.01)

(58) Field of Classification Search
CPC ........ A61B 18/20; A61B 18/22; A61B 18/24; A61B 18/28; A61B 18/201; A61B 2018/00452; A61B 2018/00464; A61M 1/0058
USPC .................. 606/9, 10, 13–17; 607/88, 89, 92; 128/898

See application file for complete search history.

(56) References Cited

U.S. PATENT DOCUMENTS

| | | | | |
|---|---|---|---|---|
| 5,102,410 | A * | 4/1992 | Dressel .......................... | 606/15 |
| 6,206,873 | B1 * | 3/2001 | Paolini et al. ..................... | 606/7 |
| 8,573,227 | B2 * | 11/2013 | Hennings et al. ............. | 128/898 |
| 2006/0224148 | A1 * | 10/2006 | Cho et al. ........................ | 606/15 |

* cited by examiner

*Primary Examiner* — Ahmed Farah
(74) *Attorney, Agent, or Firm* — Vorys, Sater, Seymour and Pease LLP; William L. Klima

(57) ABSTRACT

A handpiece and method of use for laser-assisted liposuction for melting, disrupting, and removing cellulite and adipose tissue. Electromagnetic energy is used to selectively melt or disrupt cellulite and adipose tissue and ablate the collagen in the constricting bands of connective tissue that causes the dimpled appearance of cellulite and adipose tissue, while avoiding damage to the surrounding fatty cells.

17 Claims, 10 Drawing Sheets

TREATMENT OF CELLULITE AND ADIPOSE TISSUE WITH MID-INFRARED RADIATION

RELATED APPLICATIONS

This application is a Divisional of related U.S. patent application Ser. No. 12/101,095 filed Apr. 10, 2008 entitled TREATMENT OF CELLULITE AND ADIPOSE TISSUE WITH MID-INFRARED RADIATION, which is Continuation-In-Part of related U.S. patent application Ser. No. 11/847,153 filed Aug. 29, 2007 entitled TREATMENT OF CELLULITE AND ADIPOSE TISSUE WITH MID-INFRARED RADIATION, now U.S. Pat. No. 8,256,429 issued Sep. 4, 2012, which is a Continuation-In-Part of related U.S. patent application Ser. No. 11/675,028 filed Feb. 14, 2007 entitled TREATMENT OF CELLULITE AND ADIPOSE TISSUE WITH MID-INFRARED RADIATION, now U.S. Pat. No. 8,127,771 issued Mar. 6, 2012, which is a Continuation-In-Part of related U.S. Pat. No. 7,217,265 issued May 15, 2007, application Ser. No. 11/131,577 filed May 18, 2005 entitled TREATMENT OF CELLULITE WITH MID-INFRARED RADIATION, which all are incorporated herein by reference in their entireties, and claims any and all benefits to which they are entitled therefrom.

FIELD OF THE INVENTION

This invention relates to a treatment of cellulite and adipose tissue with mid-infrared radiation, and more specifically to a method and system of selectively delivering energy to and thermally altering structures of the skin that cause the dimpled appearance of cellulite and adipose tissue.

BACKGROUND OF THE INVENTION

Cellulite is a condition of the skin characterized by the presence of hard lumps of fatty material surrounded by fibrous connective tissue that gives the skin an orange peel appearance. It is caused by degeneration of subcutaneous blood vessels and results in a thinning of the dermis and pooling of body fluids. In general, adipose tissues is fatty tissue. Cellulite and adipose tissue occurs most often on the thighs, buttocks, and upper arms of Caucasian females and is often associated with obesity.

Current treatments for cellulite and adipose tissue include mechanical massage, exercise, weight loss, diet, and topical drug treatment. None of these treatments are very effective or long lasting. There is a need for a more effective and longer lasting way to smooth the skin of people suffering from cellulite and adipose tissue.

Prior art has focused on damaging or removing the fatty tissue to cure cellulite and adipose tissue. The method may not be effective due to the fact that connecting tissue, not fat, is the true cause of cellulite and adipose tissue. Heating of the fatty cells may be beneficial to a certain degree if the cells are encouraged to metabolize fat faster. However, the appearance as a result of damaged and dead fatty cells is not attractive cosmetically unless the residue is removed in a liposuction therapy.

Other prior art teaches stimulating the generation of new collagen with a variety of optical, electromagnetic, and cosmetic means. U.S. Pat. No. 6,443,914 issued Sep. 3, 2002 to Constantino teaches the use of ultrasound to build additional fibrous tissue through the normal body repair mechanism.

U.S. Pat. No. 4,985,027 issued Jan. 15, 1991 to Dressel teaches a soft tissue aspiration device and method of use. However, the laser delivery tip of the optical fiber laser device is protected within the distal tip of the cannula, and there is no extension of the firing tip of the optical fiber beyond the distal tip of the cannula. Thus, this patent is limited to a contained tip configuration.

U.S. Pat. No. 6,470,216 issued Oct. 22, 2002 to Knowlton teaches the use of a radio frequency generator to heat and ablate sub-dermal fat and regenerate collagen for skin tightening. RF energy is known to be highly absorbed in fatty tissue, which works in the opposite way to the present invention that avoids melting fat tissue.

U.S. Pat. No. 6,673,096 issued Jan. 6, 2004 to Lach teaches the simultaneous delivery of infrared laser radiation in the range of 650 to 1295 nm and massage devices. It is specifically stated that the objective of the invention is to heat deep layers of tissue and cause lipolysis or decomposition of fatty tissue. This range of wavelengths may heat the fatty tissue but not targeting the connective collagen as in the present invention. In addition, it is not stated that any fluence levels is required and may be trying to perform bio-stimulation with low-level radiation. The present invention clearly requires adequately high fluence levels to shrink or denature collagen and does not require bio-stimulation to be effective.

U.S. Pat. No. 6,605,080 issued Aug. 12, 2003 to Altshuler et al. teaches a method of selectively targeting fatty tissue while avoiding damage to tissue for the purpose of fat removal. The present invention proposes exactly the opposite in order to alter the collagen containing connective tissue, which is the true cause of cellulite and adipose tissue. Altshuler et al. teaches that the optical absorption spectra of fatty tissue is very different from the absorption spectra of surrounding tissue because of the presence of vibrational modes in the molecules of lipids that form fatty tissue. Since both fatty tissue and water based tissue such as collagen can both be found in the same parts of the skin, the difference in these two optical absorption spectra allows a way to selectively target only one of the types of tissue while reducing the heat absorbed by the other; and henceforth preserving it. Altshuler et al. teaches only the ability to heat fat while sparing tissue. Altshuler et al. does not teach that the opposite can be applied under special conditions. Moreover, Altshuler et al. does not mention cellulite and adipose tissue in his work involved with different wavelengths.

U.S. Pat. No. 5,304,169 issued Apr. 19, 1994 to Sand and U.S. Pat. No. 4,976,709 issued Dec. 11, 1990 to Sand teach that collagen goes through several stages of alteration when heated. At temperatures lower or around 50° C., collagen is not affected. At about 60° C., collagen may contract and shrink by about 30% without denaturization or permanent damage to the structure. It has been shown that at these temperatures the shrinkage is long term and the collagen remains viable. At temperatures >65° C. however the collagen will denaturize and lose its elasticity and collapse. When this happens to a connective fiber the fiber may weaken, stretch, and possibly break.

U.S. Pat. No. 6,413,253 issued Jul. 2, 2002 to Koop et al., U.S. Pat. No. 6,451,007 issued Sep. 17, 2002 to Koop et al. and U.S. Pat. No. 5,885,274 issued Mar. 23, 1999 to Fullmer et al. teach a mid-IR laser directed to the surface of the skin with energy densities of 10 to 150 J/cm$^2$ and pulse widths of 5 to 500 msec. A pulsed cryogen cooling system is used to protect the epidermis by spraying a burst of R134a cryogen onto the treatment site immediately pre or post laser treatment.

ADVANTAGES AND SUMMARY OF THE INVENTION

The present invention relies on a combination of selective absorption by collagen in fibrous strands or connective tissue and surface cooling to prevent epidermal damage. Strands that are pulling tightly on crevasses in the skin are heated to the point of denaturization, causing them to relax, expand and release the skin outward. On the other hand, strands that connect to outward bulging areas are heated merely to the non-damaging collagen shrinkage temperature of about 65° C. so they permanently contract and help smooth the skin surface.

Lasers in the wavelength region of 1.2 µm to 1.8 µm have been used for many years to shrink and damage collagen for dermatological purposes. Altshuler specifically points out that the result of utilizing a wavelength region of 1.3 µm to 1.6 µm is extremely poor in his fat removal invention because of the poor absorption in fat within the region. Therefore, lasers in the region of 1.3 µm to 1.6 µm are very suitable to be used to selectively shrink or damage collagen in the presence of fatty tissue. The present invention recognizes this fact and combines it in a novel and unique manner with the established good collagen absorption properties of that wavelength region to make a very useful invention. This particular aspect of the present invention accomplishes the opposite of Altshuler.

The selective nature of several bands of infrared electromagnetic radiation allows the collagen to be heated without damage to the surrounding fatty tissue. A combination of selective absorption by collagen in fibrous strands and surface cooling to prevent epidermal damage enables the present invention to work. Strands that are pulling tightly on crevasses in the skin are heated to the point of denaturization, causing them to relax, expand and release the skin outward. On the other hand, strands that connect to outward bulging areas are heated merely to the non-damaging collagen shrinkage temperature of about 65° C. so they permanently contract and help smooth the skin surface.

In particular the Nd:YAG laser, when operated at a wavelength of 1.32 um, is nearly perfect to selectively damage collagen in the presence of fat. Wavelengths longer than 1.6 um will not be able to penetrate deep enough through the epidermal tissue to reach the target depth and wavelengths shorter than 1.3 um do not have enough water absorption to effectively heat the collagen strands. However, when this invention is used in a percutaneous manner utilizing a fiber optic probe, wavelengths such as 2.0 um would be very effective.

The present invention provides a system and method to shrink some of the cellulite and adipose tissue connective strands while weakening and stretching others. Strands in the valleys of the cellulite and adipose tissue dimples are stretched and weakened while strands near the upper hill, top or surface of the dimple are shrunk to pull the top of the dimple inward. Precise control of the heating temperature is critical to accomplish this simultaneously. Radiation fluence must be high (>1 J/cm$^2$) enough to cause permanent shrinkage or denaturization of the collagen in the connective tissue. Low-level fluence (<1 J/cm$^2$) will not work to break connective tissue bonds, but they may stimulate fatty tissue reduction. The improved method to accomplish this is to vary the pulse length of the laser so it will selectively cut or heat and shrink the appropriate target tissue.

The method of the present invention requires a temperature feedback device such as a thermal sensing handpiece with feedback controls that is in direct contact with treated tissue. The valleys of the cellulite and adipose tissue will be treated at a higher temperature (>70° C.) to break the strands and the tops of the hills of the cellulite and adipose tissue will be treated at a lower temperature (50 to 70° C.) to shrink the connective strands. Pulsed cryogen cooling can be used to prevent surface damage to the epidermis and allow repeated passes over the same spot to drive the heat deep. Less cooling and fluence is used to limit penetration and reduce the target temperature. The fatty tissue may be heated enough to start to metabolize faster but the selective nature of energy at a wavelength of 1320 nm passes directly through the fat to target, i.e., be absorbed by, the fibrous strands. Also, the fat is useful to maintain a smooth and healthy appearance of the skin, in contradistinction to the teachings of the prior art.

Our new invention uses variable pulse lengths of laser energy and cryogen spray to target different structures. Prior to this invention it was not known how to target and damage fibrous strands without causing extensive damage to surrounding tissue. However, by selecting an energy source that matches the transmission bands of fatty tissue and also matches the absorption bands of collagen and simultaneously varies the pulse length of the energy it is now possible to accomplish this. However, the target tissue may be much deeper in the dermis than taught in the prior art. Fibrous strands can be 1 to 5 mm deep into tissue where the target papillary dermis in prior art is only 0.3 to 0.5 mm deep. To permit penetration of the energy deep enough it may be necessary to provide multiple bursts of energy at the same spot while simultaneously cooling the epidermis to prevent damage. In one embodiment, the cooling is done in such a way that only cools the surface and not the deep target structure. One way to do this is to use a pulsed cryogen spray cooling method.

The use of multiple bursts of energy in the present application is novel and unique. The use of pulse stacking or repeated treatments in the same spot is not preferred in the prior art because of the risk of over treating. The first pulses heat the tissue enough that the subsequent pulses are sufficient to raise the skin temperature in an uncontrolled manner that causes burns and blisters to the surface. In this new invention we show a way to measure the temperature of the skin surface during the treatment pulse sequence and to control the energy source with a feedback loop so that the skin temperature never reaches damage threshold.

The energy required in this new invention must also be delivered in a much longer time period to be effective on the deeper structures. Prior art teaches the use of pulse duration of typically about 50 msec. To reach the deeper structures we must use about 500 to 2000 msec pulse width. This longer pulse width also enables the electronics of the temperature feedback system to accurately control the energy source.

The pulse width of the laser can be adjusted by the use of IGBT devices in the power supply that are able to modulate the current flow to the flashlamp in the laser cavity. The pulse length of the laser can also be modulated by the use of discrete capacitors and inductors in the pulse forming network of the power supply. The most effective pulse lengths for ablation or cutting are in the microsecond region, and are preferably between about 20 and about 100 microseconds, or more or less. This short pulse is capable of generating sufficient peak energies to generate plasma effects or photoacoustic effects at the fiber tip which have been shown to cut and ablate tissue with minimal coagulative side effects.

Effective pulse lengths for connective tissue shrinking or coagulating are in the millisecond region, preferably between about 0.5 and about 50 milliseconds, or more or less. These long pulses will not generate plasma effects or photoacoustic effects at the fiber tip but will gently heat and shrink collagen in the connective collagen tissue.

The present invention is utilized inserting a fiber optic energy delivery probe into the skin at the location of the fibrous strands and treating them directly. The use of fiber optic delivery systems for laser energy is well known in the industry, but the use of this technique with a selectively absorbing energy source to treat cellulite and adipose tissue is not obvious. Prior attempts to try this have used energy sources that did not distinguish between the collagen and the fat and the result was extensive damage to all the surrounding tissue and a poor cosmetic result. An additional improvement to this percutaneous approach is to use a fiber optic probe that directs the energy out the front or side of the distal end. This allows the probe to be placed along side the connective strands under the skin and cut in a line with the energy pointed away from the skin surface. It is also possible to perform this procedure under ultrasound imaging to more accurately locate and cut the connective strands. The use of energy in the range of 1.3-1.6 µm or 1.9 to 2.2 µm allows the strands to be cut without affecting the surrounding fatty tissue. In this embodiment the use of the more highly absorbing 2.0-3.0 um radiation such as produced by a Thulium, Holmium, or Erbium doped YAG crystal may be more appropriate as the use of a percutaneous fiber optic makes it unnecessary to optically penetrate the epidermis to reach the target tissue.

Lasers that could be used for this invention include Nd:YAG at 1320 nm, Diode lasers at 1450 nm, ER:Glass laser at 1540 nm, fiber lasers at 1550-1600 nm, Holmium or Thulium lasers at 1.9-2.2 um or Erbium lasers at 2.9 um.

It is yet a further object and advantage of the present invention to provide a method for treating cellulite and adipose tissue by moving the end of the optical fiber past the end of a cannula so that heat does not impinge on the needle tip and heat it up. In one embodiment, the smooth and optionally blunt end of the cannula, rather than sharpened piercing tip, prevents inadvertent puncture of skin and is safer overall to use. The apparatus includes a relatively stiff or rigid polyimide coated optical fiber, optionally cleaved flat or at an angle, providing the advantage of not requiring the use of the cannula and resistance by the fiber to breakage particularly during placement or use. By extending the firing tip of the fiber optic past the distal end of the cannula, the firing tip is well beyond the cannula and there is no risk of overheating the cannula. The fiber can also be made of sapphire crystal. This material is strong enough to not break in the tissue and can transmit laser wavelengths in the 3 um band such as the Erbium YAG laser at 2.94 um.

The coating is made of a material which absorbs the laser energy at the wavelength utilized. During use, it is an advantage to cause the distal end of the coating to burn to a char during laser delivery. The char heats to a very high temperature and acts as a hot tip ablation device, having a hat, ablative cutting surface. In an embodiment of the present invention, the method using a pulsed laser in conjunction with a coated fiber such that the rapid temperature rise at the charred fiber tip causes an acoustic explosion which ablates and disrupts tissue.

The tip of the fiber can be extended beyond or past the end of the cannula tip so that it is no longer adjacent the cannula tip, increasing maneuverability and improving the efficiency of the cutting tip. Additionally, by moving the distal tip of the optical fiber well past the tip of the cannula there is less chance that the metal cannula will be heated by the laser beam exiting from the emitting face of the fiber, it provides an advantage to minimize heating of the tip of the cannula which if heated may cause burns to the patient's skin as it is introduced and/or withdrawn before, during or after use. Having the fiber in direct contact with treated tissue allows much higher power density and faster ablation. Moreover, the laser energy from the fiber is distributed more uniformly into the target tissue compared to side-firing cannulae. Also, it allows simultaneous effect of fat ablation and heating of tissue to cause collagen contraction or collagen stimulation.

Removing melted fat, tissue and blood during treatment by the integral suction system enables higher laser ablation efficiency.

A thermal sensor inserted in the cannula allows continuous real time thermal feedback at the precise location of treatment. Real time feedback allows more precise thermal monitoring and control of laser intensity to avoid harmful damage to patient. Compared to the non-contact thermal sensor that can only detect skin temperature, the present apparatus and method is more precise and insensitive to variation in skin thickness, density and surrounding temperature.

It is also an object and advantage of the invention to use a Touhy Borst clamp on the fiber as a marker to guarantee that the fiber is well beyond the cannula tip. Using an aiming beam up to 10 times or more brighter than the conventional aiming beam, the practitioner can easily determine exactly where the fiber tip is and be able to move it well past the cannula tip before firing it to ablate the undesirable connective tissue.

Objects and advantages of the present invention, therefore, include but are not limited to the following:

1. The fiber assists in advancing the cannula by cutting through fibrous strands.
2. Suction on the cannula is activated as the cannula is advanced, pushing it into the fat melted by the protruding fiber. Thus, fat will be liquefied prior to entering the cannula then aspirated or suctioned out through the vacuum delivery and waste disposal aspiration tube. Additionally, the heat is delivered to tighten the overlying skin.
3. Melted fat is detected by increased popping sound of the pulsed laser which indicates that it is time to activate suction and remove the excess liquid fat to allow higher laser ablation efficiency.
4. Having the fiber protrude out the end allows the simultaneous effect of fat ablation and of heating tissue to cause collagen contraction or collagen stimulation. This would be impossible with an enclosed fiber.
5. A special Teflon bushing at the tip of the cannula will prevent damage to the fiber as it protrudes out the hole in the tip.
6. A polyimide coated fiber can be used in conjunction with a suction cannula with a hole in the end, the advantage being that the hole can be made very small and the fiber will not obstruct the flow of fat suctioned into the cannula.

Thus, the present device and method of use improves the outcome of conventional liposuction in small areas such as the neck, chin and arms and now is fast enough to be effectively used on larger areas such as the abdomen and thighs.

Further objects and advantages of the present invention will be come apparent through the following descriptions, and will be included and incorporated herein.

DETAILED DESCRIPTION OF THE EMBODIMENT

Figure 1:
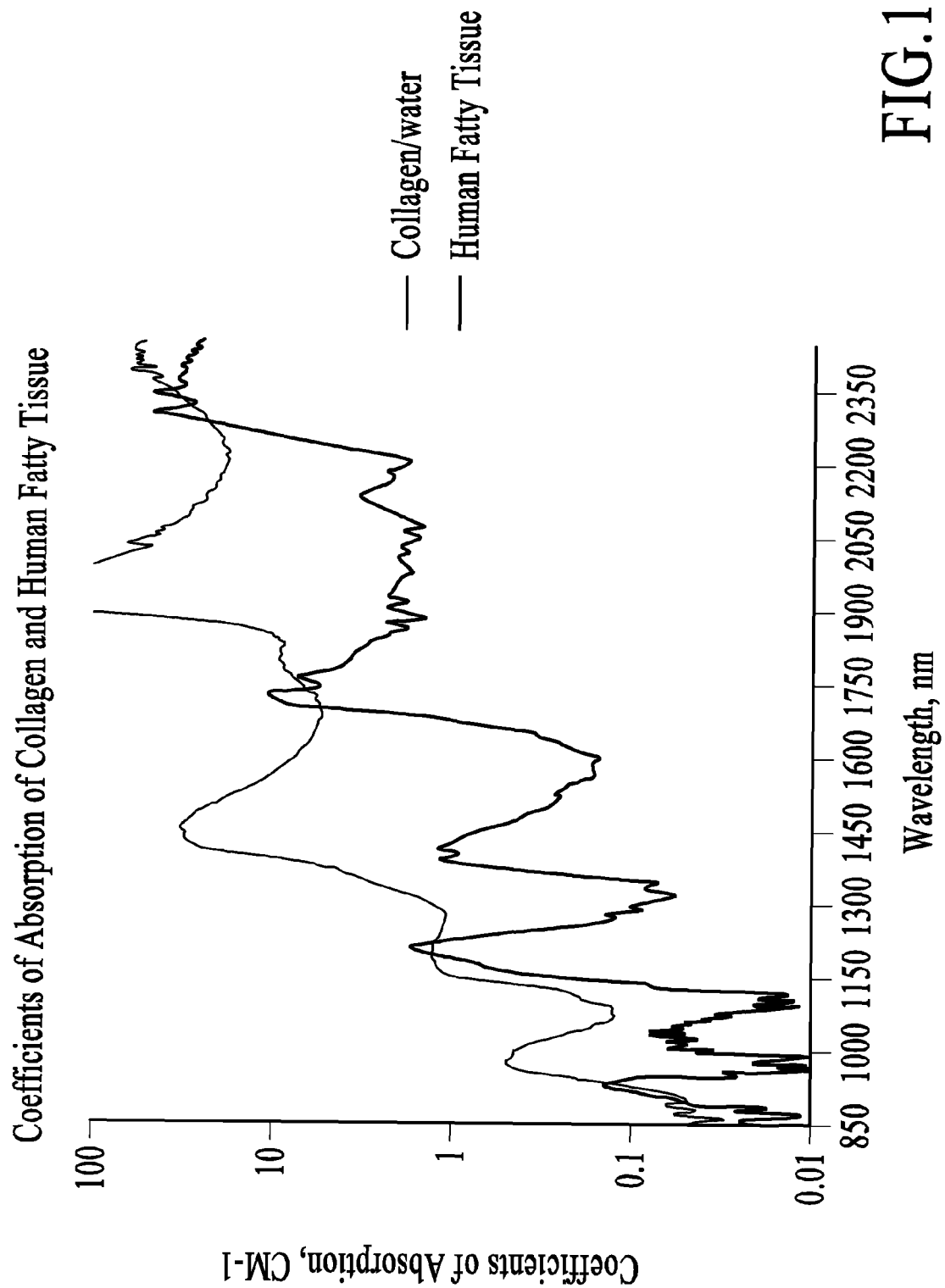
FIG. 1 is a graph illustrating the infrared absorption curves of collagen/water and human fatty tissue 124.

The description that follows is presented to enable one skilled in the art to make and use the present invention, and is provided in the context of a particular application and its requirements. Various modifications to the disclosed embodiments will be apparent to those skilled in the art, and the general principals discussed below may be applied to other embodiments and applications without departing from the scope and spirit of the invention. Therefore, the invention is not intended to be limited to the embodiments disclosed, but the invention is to be given the largest possible scope which is consistent with the principals and features described herein.

It will be understood that in the event parts of different embodiments have similar functions or uses, they may have been given similar or identical reference numerals and descriptions. It will be understood that such duplication of reference numerals is intended solely for efficiency and ease of understanding the present invention, and are not to be construed as limiting in any way, or as implying that the various embodiments themselves are identical.

DEFINITIONS

An "absorption coefficient" of a substance is a measure of the fraction of incident light that is absorbed when light is passed through the substance. The absorption coefficient (typically in units of cm.sup.-1) varies with the nature of the absorbing substance and with the wavelength of the light.

"Collagen" as used herein refers to any of the several types of collagen.

Collagen biosynthesis is said to be "inhibited' when cells treated with the claimed methods secrete collagen at a rate that is less than about 70% of that of untreated cells. Preferably, treated cells secrete collagen at a rate that is less than about 50%, and more preferably less than about 30% of the rate at which untreated cells secrete collagen.

Collagen biosynthesis is said to be 'stimulated' when cells treated with the claimed methods secrete collagen at a rate that is greater than about 110% of the rate at which untreated cells synthesize collagen. Preferably, treated cells secrete collagen at a rate that is about 150%, and more preferably greater than about 200% greater than that of untreated cells.

"Monochromatic" light is of one wavelength or a narrow range of wavelengths. If the wavelength is in the visible range, monochromatic light will be of a single color. As used herein, "monochromatic" refers to light that has a bandwidth of less than about 100 nm. More preferably, the bandwidth will be less than about 10 nm, and most preferably less than about 1 nm.

"Non-coherent light energy" is light that is non-laser. Unlike laser light, which is characterized by having its photon wave motions in phase, the wave motions of the photons that make up non-coherent light are in a randomly occurring phase order or are otherwise out of phase.

A "wound" as used herein, refers to any damage to any tissue in a living organism. The tissue may be an internal tissue, such as the stomach lining or a bone, or an external tissue, such as the skin. As such, a wound may include, but is not limited to, a gastrointestinal tract ulcer, a broken bone, a neoplasia, and cut or abraded skin A wound may be in a soft tissue, such as the spleen, or in a hard tissue, such as bone. The wound may have been caused by any agent, including traumatic injury, infection or surgical intervention.

A "growth factor" as used herein, includes any soluble factor that regulates or mediates cell proliferation, cell differentiation, tissue regeneration, cell attraction, wound repair and/or any developmental or proliferative process. The growth factor may be produced by any appropriate means including extraction from natural sources, production through synthetic chemistry, production through the use of recombinant DNA techniques and any other techniques, including virally inactivated, growth factor(s)-rich platelet releasate, which are known to those of skill in the art. The term growth factor is meant to include any precursors, mutants, derivatives, or other forms thereof which possess similar biological activity(ies), or a subset thereof, to those of the growth factor from which it is derived or otherwise related.

FIG. 1 is a graph illustrating the infrared absorption curves of collagen/water and human fatty tissue 124. The graph illustrates the coefficient of absorption (CM-1) of collagen and of human fatty tissue 124 as a function of wavelength respectively. As shown in FIG. 1, the optical absorption spectra of fatty tissue 124 is very different from that of collagen because of the presence of vibrational modes in the molecules of lipids that form fatty tissue 124. The coefficient of absorption of human fatty tissue 124 is extremely low in the wavelength region of 1.3 µm to 1.6 µm indicating poor absorption in fat within the region. The peak coefficient of absorption of fatty tissue 124 absorbing bands are 0.90µ-0.93 µm, 0.119 µ-0.122 µm, and 0.17 µm-0.173 µm. However, as also shown in FIG. 1, the coefficient of absorption of water-based collagen is relatively high in the wavelength region of 1.3 µm to 1.6 µm indicating good infrared absorption. The system 100 of present invention combines this understanding with the established high coefficient of absorption of collagen in that wavelength region. Therefore, lasers having output in the region of between about 1.3 µm and about 1.6 µm and between about 1.9 um and about 2.2 um are very suitable to selectively shrink or denaturize collagen containing connective tissue 122 in the presence of fatty tissue 124.

Figure 2:
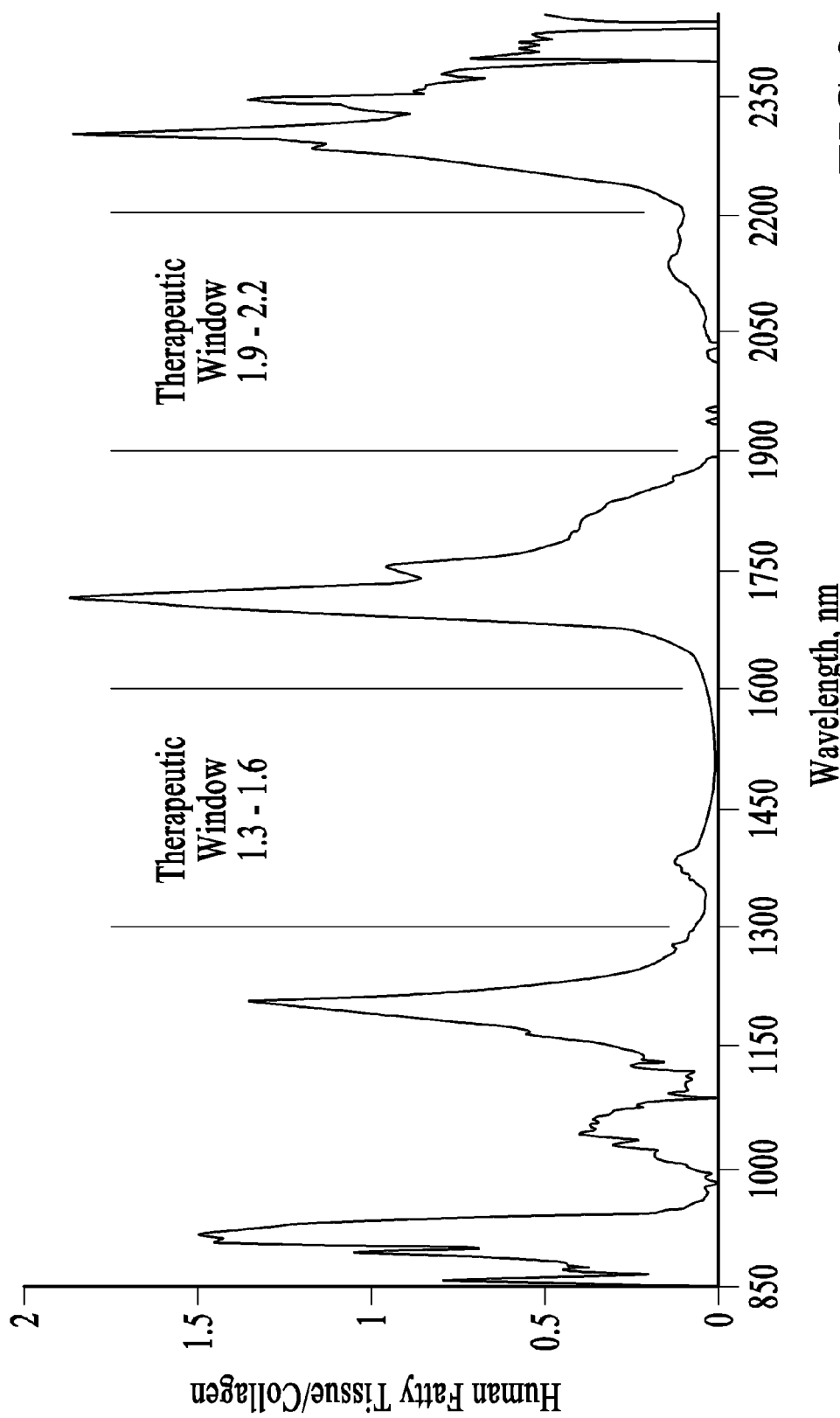
FIG. 2 is a graph illustrating the ratio of the coefficients of infrared absorption of human fatty tissue 124 and collagen as a function of wavelength.

FIG. 2 is a graph illustrating the ratio of the coefficients of infrared absorption of human fatty tissue 124 and collagen as a function of wavelength. As indicated, the higher the ratio, the larger the difference between infrared absorption of fatty tissue 124 and that of collagen; and vice versa. As shown in FIG. 2, there are windows where the ratio between fatty tissue 124 and collagen is the lowest, these are called "therapeutic windows". "Therapeutic windows" indicate the range of wavelengths where collagen containing connective tissue 122 may be effectively targeted with minimal damage to fatty tissue 124. As shown in FIG. 2, these windows occur in the wavelength range of 1.3 µm-1.6 µm and 1.9 µm-2.2 µm respectively. Wavelengths around 3 um are highly absorbed in both fat and tissue and can be used to cut tissue located directly in front of the fiber probe.

Figure 3:
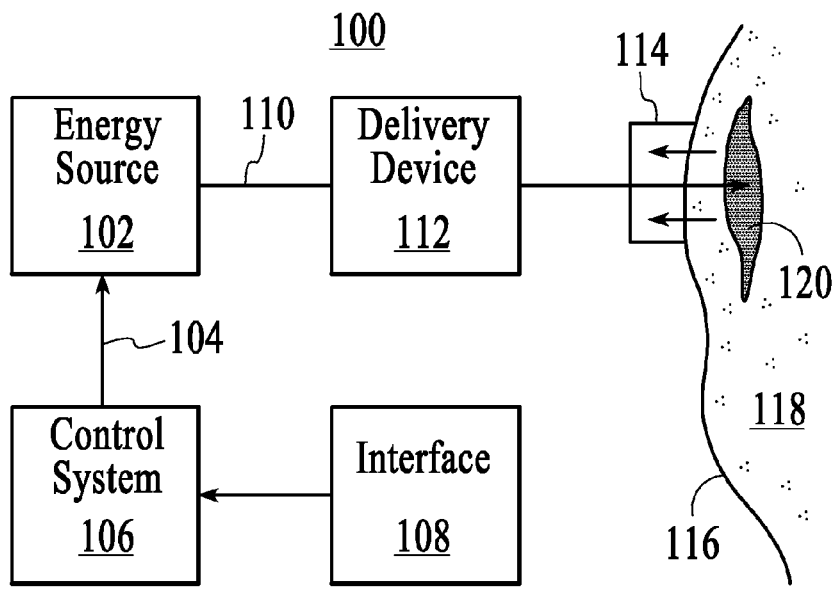
FIG. 3 is a representative schematic block diagram of an embodiment of a cellulite and adipose tissue treatment system 100 of the present invention.

FIG. 3 is a representative schematic block diagram of one embodiment of a cellulite and adipose tissue treatment system 100 of the present invention. Operation of energy source 102 to produce energy for delivery by the system 100 is controlled according to control signal 104 from control system 106. Control system 106 includes a physician interface 108 for operating the system. Said interface 108 optionally includes a footswitch (not shown) for energy delivery, display and interactive and/or menu driven operation utilizing operator input, prompts, etc. Additional energy delivery control interface means shall be known to those skilled in the art.

The energy source 102 can be a laser that emits in the region of 1.3 µm-1.6 µm or it can be a broad-spectrum source such as a filament lamp, flashlamp or other white light source that has energy output in the region of 1.3 µm-1.6 µm. The use of a device described by Fullmer in U.S. Pat. No. 5,885,274 would be ideal for the cellulite and adipose tissue treatment system 100 of present invention because of the large percentage of energy from a filament lamp that is present in the infrared. However, to be most effective and to spare fatty tissue 124, the white light source should be filtered using absorbing or dielectric filters so the peak fatty tissue 124 absorbing bands of 0.90 µm-0.93 µm, 0.19 µm-0.22 µm, and 1.7 µm-1.73 µm are not included. The prior art teaches the use of white light to treat cellulite and adipose tissue does not suggest filtering these wavelengths out of the spectrum. The mechanism of action of this prior art is to raise the temperature of the fatty tissue 124 to 42° C. so that fat cells 124 metabolize fat; resulting to a reduction of appearance of cellulite and adipose tissue.

Figure 5:
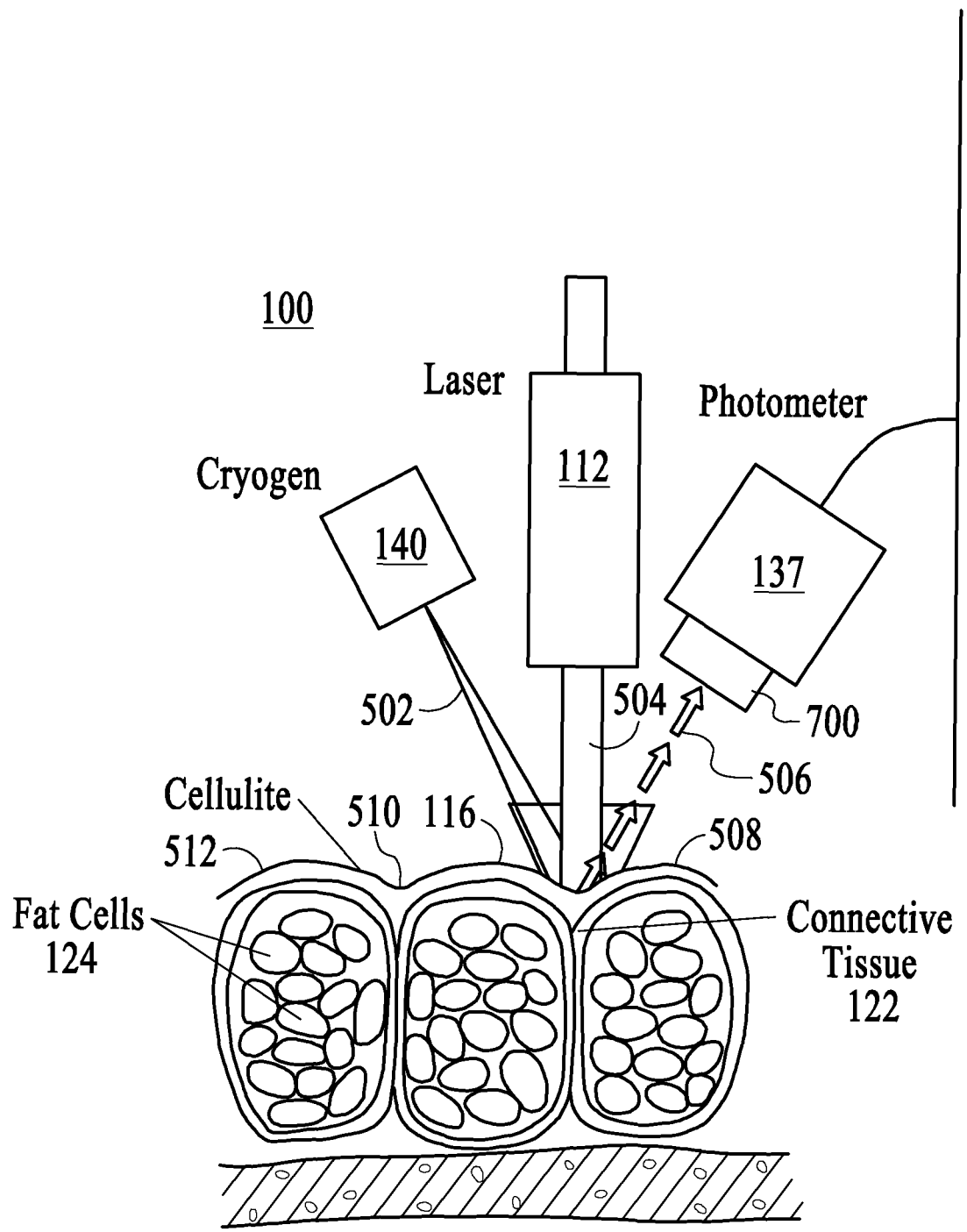
FIG. 5 is a representative detail schematic diagram of an embodiment of the cellulite and adipose tissue treatment system 100 of the present invention.
Figure 6:
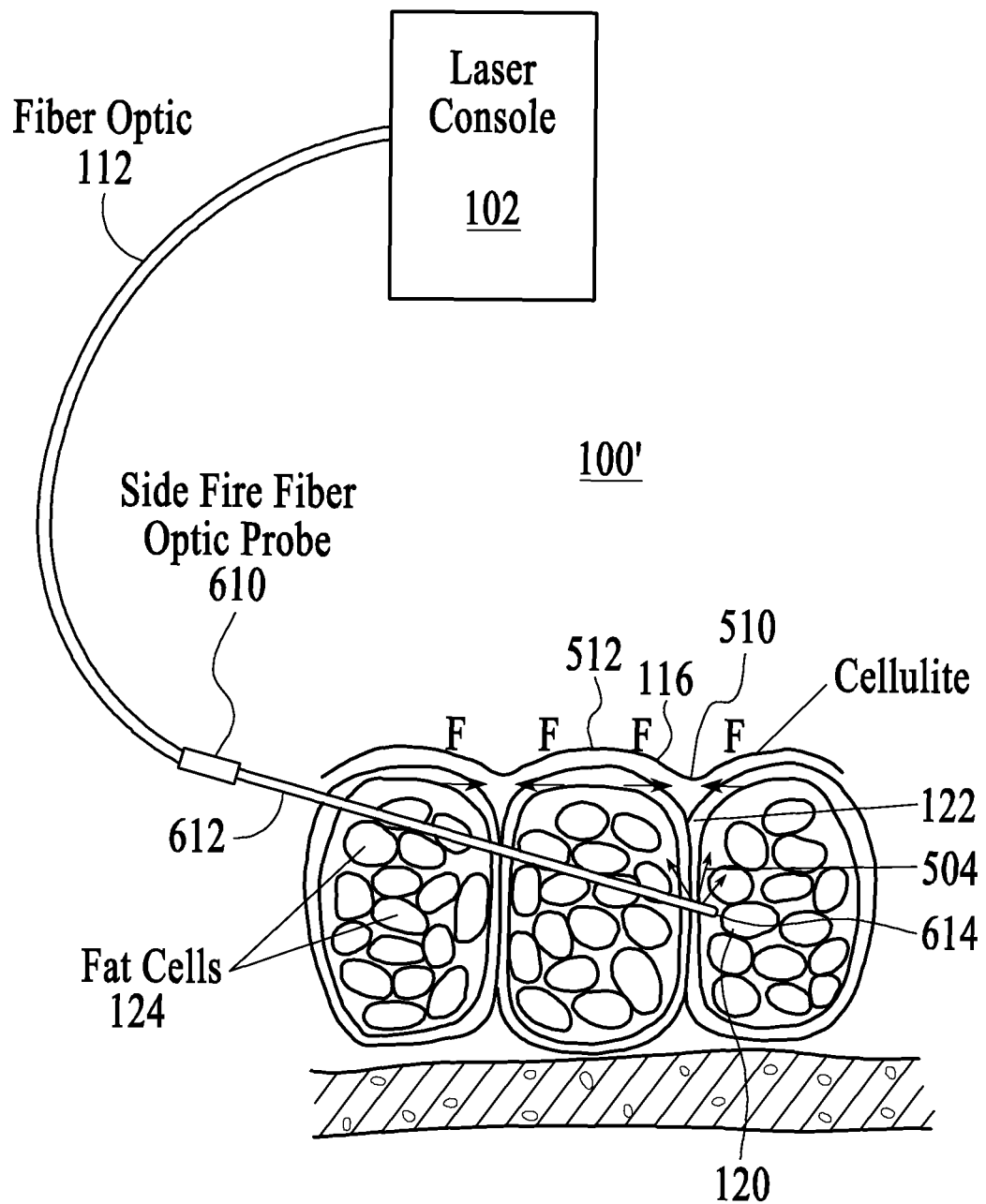
FIG. 6 is a representative detail schematic diagram of an alternative embodiment of the cellulite and adipose tissue treatment system 100' of the present invention.

In one embodiment, energy source 102 can be a neodymium doped yttrium-aluminum-garnet (Nd:YAG) laser, energized by a flash-lamp or laser diode, at 1.32 µm, diode lasers at 1.45 µm, ER: Glass laser at 1.54 µm and fiber lasers at 1.55-1.60 µm. Energy source 102 is controlled by control system 106 which comprises the software and electronics to monitor and control the laser system, and graphical user interface 108. The beam of laser energy 110 from the energy source 102 is directed into a delivery device 112 which may be an optical fiber, a fiber bundle or articulated arm, etc. In the case of an Nd:YAG laser operated at a wavelength of 1.32 µm, it is extremely effective to selectively damage collagen containing connective tissue 122 in the presence of fat tissue 124. As best shown in FIGS. 1, 2 and 5, fatty tissue 124 may be heated enough to start to metabolize faster but the selective nature of Nd:YAG laser at 1.32 µm will allow most of the energy to transmit directly through the fatty tissue 124 to target the fibrous strands of connective tissue 122. Wavelengths longer than 1.6 µm will not be able to penetrate deep enough through the surface tissue 116 to reach the target tissue or structure 120 and wavelengths shorter than 1.3 µm do not have enough coefficients of absorption of collagen to effectively heat the collagen strands of connective tissue 122. However, as best shown in FIG. 6, wherein system 100 of the present invention is used in a percutaneous manner utilizing a fiber optic probe 610, wavelengths in the range of 2.0 µm would be very effective.

Control system 106 ensures adequate energy is delivered deep into dermis while protecting epidermis. Modern instruments to provide dynamic cooling of the surface layers of tissue or other materials are well suited to these applications. A coolant spray can be provided through a handpiece or it could be provided with another separate device. Finally, a connection to a computer and the control system 106 of the energy source 102 will allow the system 100 to utilize electronic or other thermal sensing means 700 and obtain feedback control signals for the handpiece. An optimum cooling strategy might be one that uses a post-irradiation cooling spurt that provides cooling or dissipation of the epidermal heat generated by absorption of energy in the non-isotropic skin, optionally containing various pigmentation levels. An appropriate cryogen spray 502 would be liquid nitrogen or tetrafluoroethane, $C_2H_2F_4$, an environmentally compatible, non-toxic, non-flammable freon substitute. In clinical application the distance between the aperture of the spray valve and the skin surface should be maintained at about 20 millimeters.

In one embodiment of the present invention, upon delivery of laser energy 110 onto the surface 116 and therethrough, the target tissue 120 will be raised to the optimal treatment temperature and generally not any higher, in an adequately rapid process, with the surface 116 temperature of the skin remaining at a temperature below the threshold for damage temperature. It will be understood that the threshold for damage temperature is the temperature below which the skin or other tissue can be elevated without causing temporary or permanent thermal damage, and above which the tissue may undergo either transient or long term thermally induced physiological change.

In an alternate embodiment of the present invention, surface cooling apparatus 114 such as a sapphire plate, convective or conductive cooling plate or other equivalent and efficient heat transfer mechanism may be employed to accurately control the temperature of the surface 116 of the epidermis.

Figure 4:
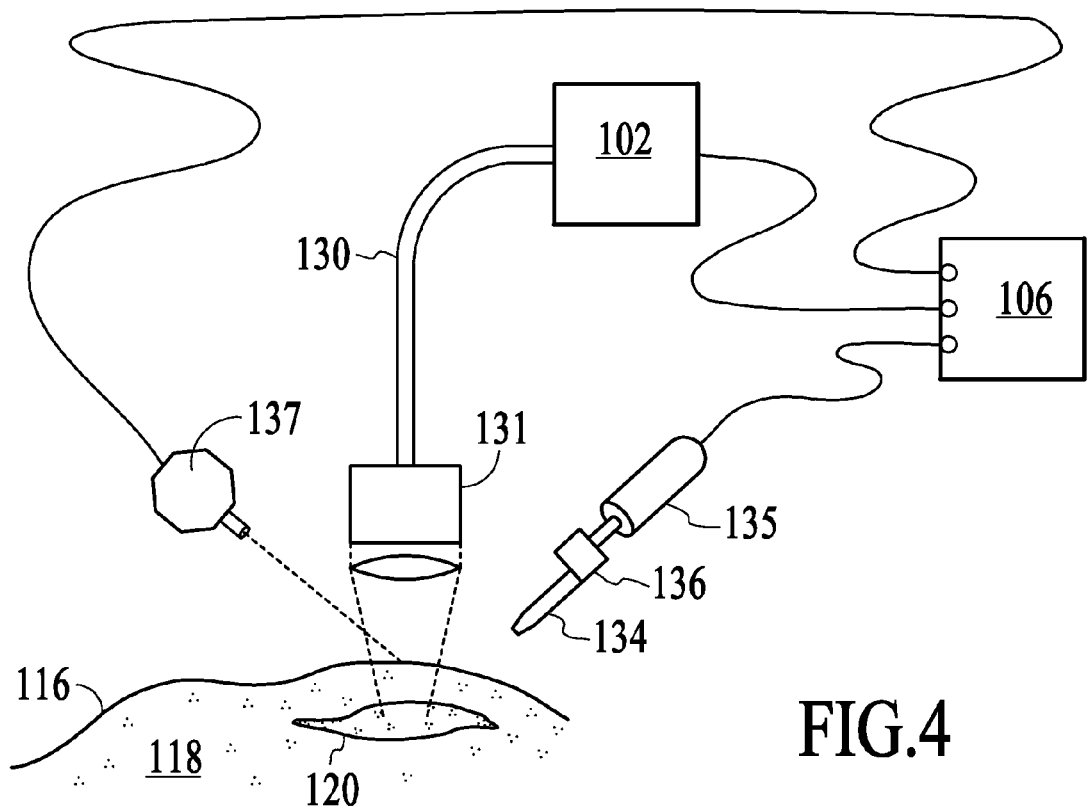
FIG. 4 is a representative schematic configuration diagram of an embodiment of the cellulite and adipose tissue treatment system 100 of the present invention.

FIG. 4 is a representative schematic configuration diagram of one embodiment of the cellulite and adipose tissue treatment system 100 of the present invention. The laser energy 110 from the energy source 102 is directed into delivery device 112 via a delivery channel 130 which may be a fiber optic, articulated arm, or an electrical cable etc. At the distal end of delivery device 112 is an energy directing means 131 for directing the pulsed energy 504 toward the surface tissue 116 and overlaying tissue 118 overlaying the target tissue or structure 120. The directing means 131 can optionally be constructed of a lens, other focusing element, lens array or other focusing configuration. A nozzle 134 is useful for directing coolant from reservoir 135 to the tissue 118, and a valve 136 for controlling the coolant interval. A visualization beam and/or temperature sensor 137 may be used to visualize target tissue 120 and/or monitor the temperature rise of the target tissue 120. Control system 106 monitors the temperature signal from sensor 137 and controls valve 136 and energy source 102. Reservoir 135 may be in the delivery device 112 or elsewhere, and contains a refrigerant 502 which may be applied to surface tissue 120 by spraying said refrigerant 502 from cooling nozzle 134 in conjunction with delivery of pulsed treatment energy 504 to the patient.

FIG. 5 is a representative detail schematic diagram of one embodiment of the cellulite and adipose tissue treatment system 100 of the present invention. The function of the delivery device 112 is to deliver mid-infrared radiation in the selective wavelength "therapeutic window" to treat sub-dermal connecting tissue 122 and also include pulsed cryogen cooling and thermal feedback.

A beam of mid infrared laser energy 504 is directed to the surface of the skin 116 with energy densities of 10 to 150 $J/cm^2$ and pulse widths of 5 to 500 msec. A pulsed cryogen cooling system 140 is used to protect the epidermis by spraying a burst of R 134a cryogen 502 onto the treatment site 508. The treatment system 100 of present invention builds on this practice. As shown in FIG. 5, multiple bursts of laser energy 504 such as Nd:YAG at 1.32 µm and cryogen spray 502 target and damage connective tissue 122 of fibrous strands without causing extensive damage to surrounding fatty tissues 124. By selecting an appropriate energy source 102 as best shown in FIGS. 1 and 2, that matches the transmission bands of fatty tissue 124 and the absorption bands of collagen, connective tissue 122 of fibrous strands can be targeted selectively without causing extensive damage to surrounding fatty tissues. Moreover, target tissue 120 of treatment system 100 of the present invention is much deeper in the dermis than that of the Koop and Fullmer patents intended. Fibrous strands 122 can be 1 mm to 5 mm deep into tissue where the target papillary dermis in prior art is only 0.3 to 0.5 mm deep. In order to address the depth issue that was not taught in prior art, it is necessary to provide multiple bursts of laser energy 504 at the same treatment site 508 while simultaneously cooling the epidermis to prevent damage by spraying cryogen 502. The cooling must be done in a way that only the skin surface 116 is cooled and not the deep target tissue 120. The task is done by using a pulsed cryogen spray cooling method that is mentioned in prior art.

As discussed, prior art does not teach multiple bursts of laser energy 504 for treatment purposes. In fact, the use of pulse stacking or repeated treatments in the same treatment site 508 is disfavored because of the risk of over treating. Theoretically, the first pulses heat the tissue enough that the subsequent pulses are sufficient to raise the skin temperature to an uncontrolled manner that could cause burns and blisters to the skin surface 116.

As shown in FIG. 5, the treatment system 100 of present invention has a non contact temperature sensor 700 set up in a way that measures the temperature of the skin surface 116 during the treatment pulse sequence and to control the energy source 102 with a feedback loop so that the skin temperature 506 never reaches damage threshold.

Moreover, the laser energy 504 required in the treatment system 100 of present invention must also be delivered in a much longer time period than 50 msec. In the present invention, order to reach the deeper structures effectively as required by treatment system 100 of the present invention, the pulse duration should be in the range of about 500 msec to 2000 msec pulse width. The longer pulse width also enables the electronics of the temperature feedback system 700 to accurately control the energy source 102.

Collagen goes through several stages of alteration when heated. At temperatures lower or around 50° C., collagen is not affected. At about 60° C., collagen may contract and shrink by about 30% without denaturization or permanent damage to the structure. It has been shown that at these temperatures the shrinkage is long term but the collagen remains viable. At temperatures greater than 65° C. however the collagen will denaturize and lose its elasticity and simply collapse. When this happens to a collagen containing connective fiber 122, the connective tissue 122 may weaken, stretch, and possibly break.

A principle of treatment system 100 of the present invention is to selectively shrink some of the cellulite connective tissue 122 while weakening and stretching others; all while neighboring fatty tissue 124 is avoided. As shown best in FIG. 6, multiple bursts of pulsed energy 504, which is ultimately from appropriate energy source 102 that compares and optionally matches the transmission bands of fatty tissue 124 and the absorption bands of collagen, are directed to target tissue 120. The pulsed energy 504 heats up connective tissue strands 122 in the valleys 510 of the cellulite and adipose tissue dimples to the temperature range of 70° C. plus so they are stretched and weakened. At the same time, connective tissue strands 122 comprising the hill top surface 512 of the cellulite and adipose tissue dimples are heated to the temperature range between 50° C. and 60° C. so they are shrunk to a certain degree. As a result, there is an inward pull in the direction indicated as F generated at the top of the dimples 512, collectively the appearance of cellulite and adipose tissue is eliminated and skin surface 116 is smoothed. The fatty tissue 124 may be heated enough to start to metabolize faster but the selective nature of laser energy 504 such as Nd:YAG at 1.32 µm will allow most of the energy to transmit directly through the fat tissue 124 to target the collagen containing connective fibrous strands 122. Also, the fat tissue 124 is needed to maintain a smooth and healthy appearance of the skin. As opposed to methods and systems of the prior art, fatty tissue 124 is spared during cellulite and adipose tissue treatment of the present invention.

FIG. 6 is a representative detail schematic diagram of an alternative embodiment of the cellulite and adipose tissue treatment system 100' of the present invention. As shown, the laser energy 110 from the energy source 102 is directed into delivery device 112 which may be a fiber optic, articulated arm, or an electrical cable etc. At the distal end of delivery device 112 is a front or side fire fiber optic probe 610 for directing the laser energy 504 inside the target tissue 120. The front or side fire fiber optic probe 610 includes a long cannula 612 for easy access and a forward or side-firing tip 614 for safe treatment, which may optionally comprise mechanical breaking of the fibers when in contact.

In one embodiment, a fiber optic probe 610 is inserted into the target tissue 120 at the location of the connective fibrous tissue 122. Multiple bursts of laser energy 504, which are from appropriate energy source 102 that matches the transmission bands of fatty tissue 124 and the absorption bands of collagen, are emitted and treat connective fibrous tissue 122 directly. The use of fiber optic delivery systems for laser energy is well known within the industry, but the use of this technique with a selectively absorbing energy source to treat cellulite and adipose tissue is not obvious. Prior attempts to try this have used energy sources that did not distinguish between the collagen and the fat and the result was extensive damage to all the surrounding tissue and a poor cosmetic result. An additional improvement to this percutaneous approach is to use a fiber optic probe 610 that directs the energy out the front or side of the forward or side-firing tip 614. This allows the probe 610 to be placed along side the connective strands 122 under the skin surface 116 and cut in a line with the pulsed energy 504 pointed towards the skin surface 116. In one alternative embodiment, it is also possible to perform this procedure under ultrasound imaging to more accurately locate and treat the connective strands 122, such as those located in the valleys 510 between the dimples of the cellulite and adipose tissue as opposed to those located in the surface tissue 512 of the cellulite tissue. The use of energy in the range of 1.3 µm-1.6 µm or 1.9 µm to 2.2 µm allows the connective tissue 122 to be treated without affecting the surrounding fatty tissue 124. In one embodiment, the use of a more highly absorbing 2.0 µm laser energy 110 such as produced by a Thulium or Holmium doped YAG crystal may be more appropriate as the use of a percutaneous fiber optic makes it unnecessary to optically penetrate the epidermis to reach the target tissue 120.

Figure 7:
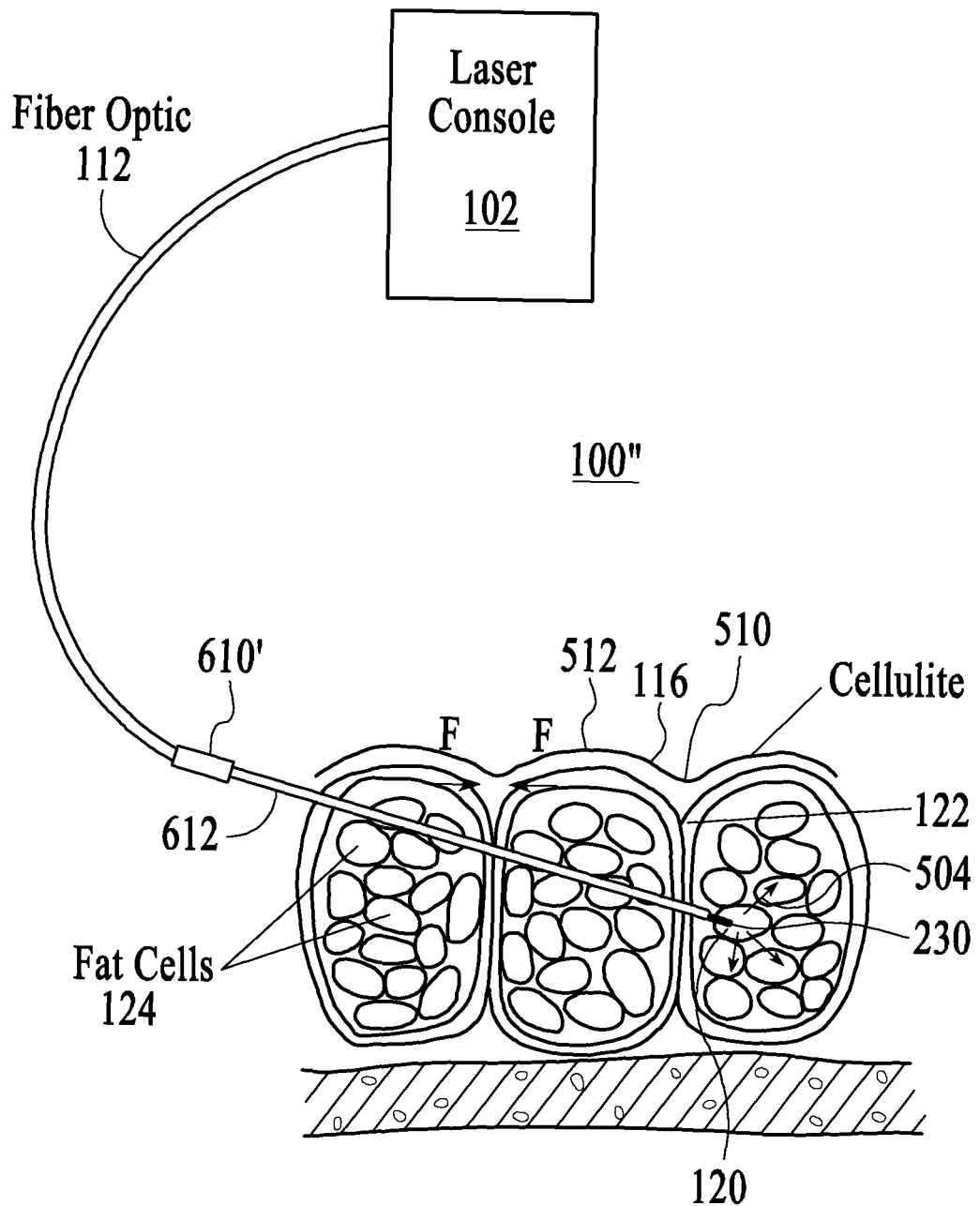
FIG. 7 is a representative detail schematic diagram of another alternative embodiment of the cellulite and adipose tissue treatment system 100" of the present invention.

FIG. 7 is a representative detail schematic diagram of another alternative embodiment of the cellulite and adipose tissue treatment system 100″ of the present invention. As shown, the laser energy 110 from the energy source 102 is directed into delivery device 112′ which may be a fiber optic, articulated arm, or an electrical cable etc. At the distal end of delivery device 112′ is a front fire fiber optic probe 610′ for directing the pulsed energy 504 inside the target tissue 120. The front fire fiber optic probe 610′ is protected by a long sheath or cannula 612′ for easy access. The optical fiber delivery device 612′ has a forward-firing firing tip 230 for safe laser treatment, which may optionally comprise mechanical disruption or breaking of the collagen fibers 122 or other target tissue 120 when in contact therewith.

Figure 8:
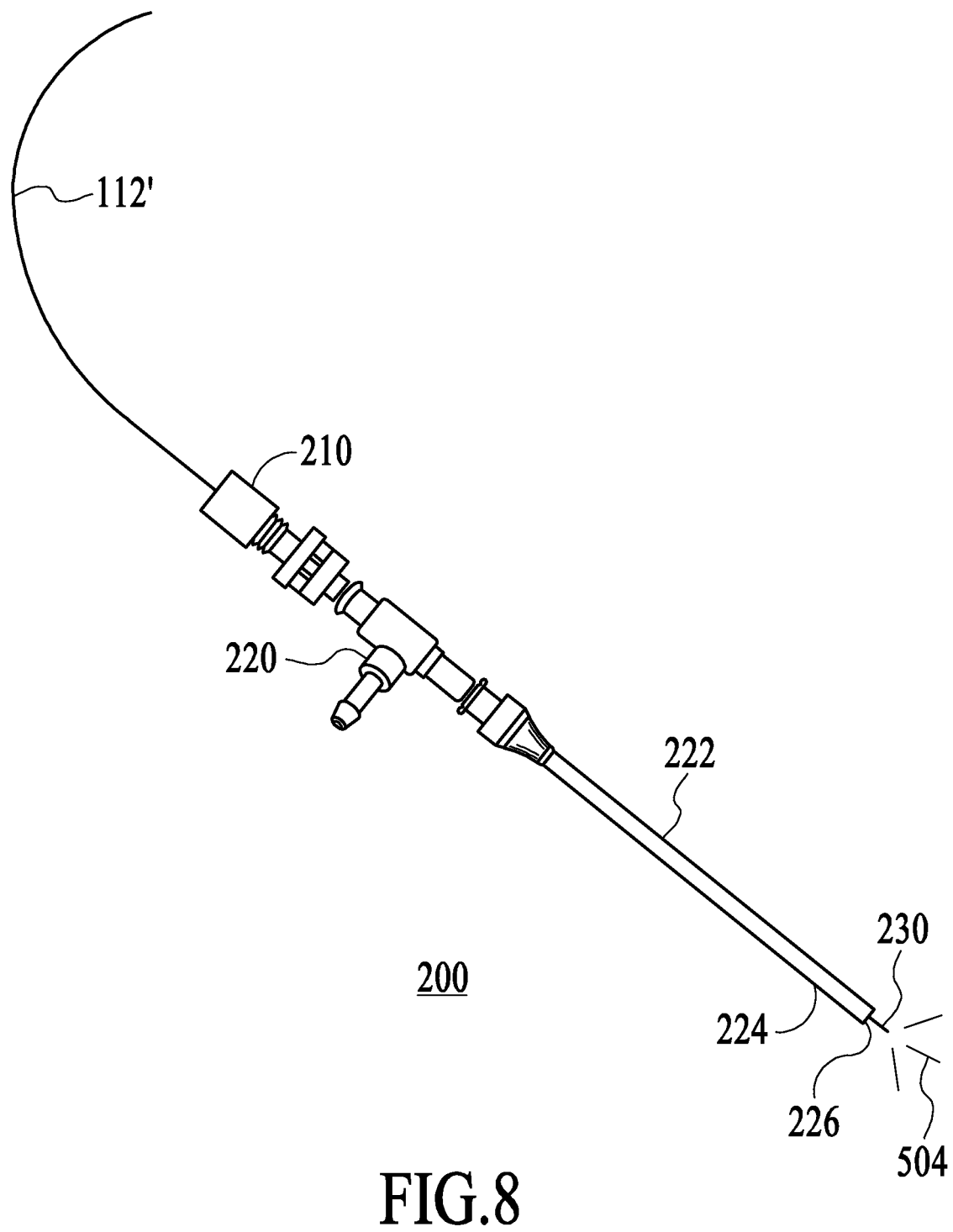
FIG. 8 is a representative detail isometric drawing of an embodiment of the cellulite and adipose tissue treatment system 200 of the present invention.
Figure 9A:
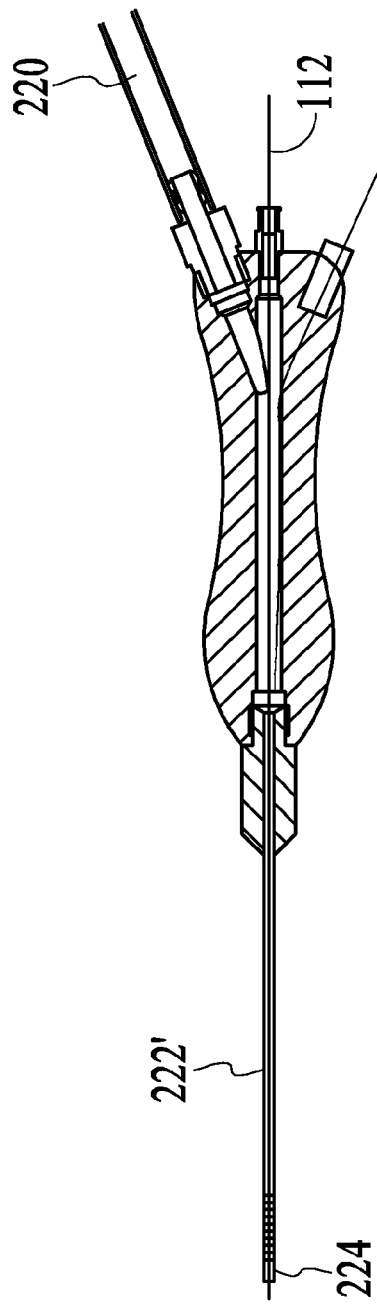
FIG. 9A is a representative detail drawing of an alternative embodiment of the cellulite and adipose tissue treatment system 200' of the present invention.
Figure 9B:
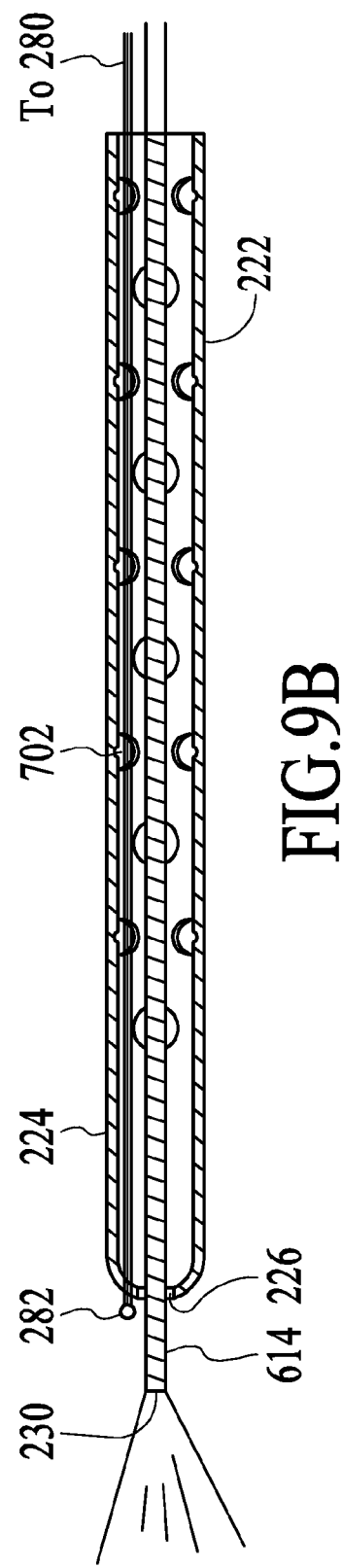
FIG. 9B is a detail view of an alternative embodiment of the cellulite and adipose tissue treatment system 200' of the present invention.
Figure 10A:
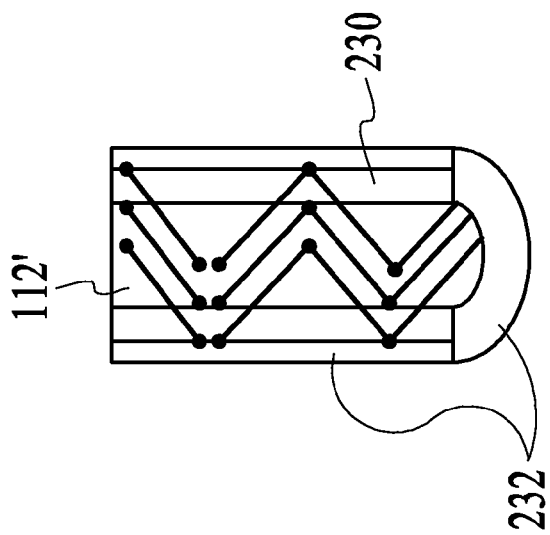
FIGS. 10A, 10B and 10C are representative section views of an embodiment of the fiber tip 230 best shown in FIGS. 8, 9A and 9B.
Figure 10B:
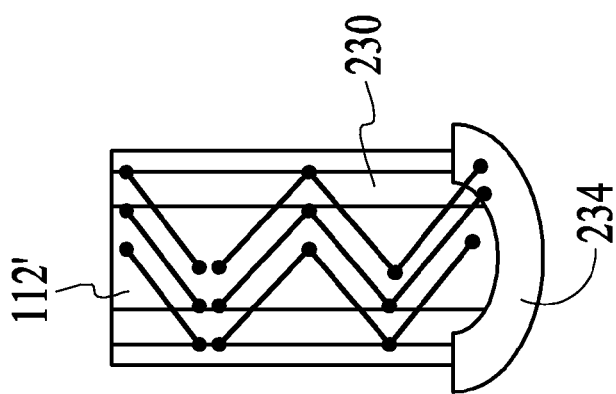
Figure 10C:
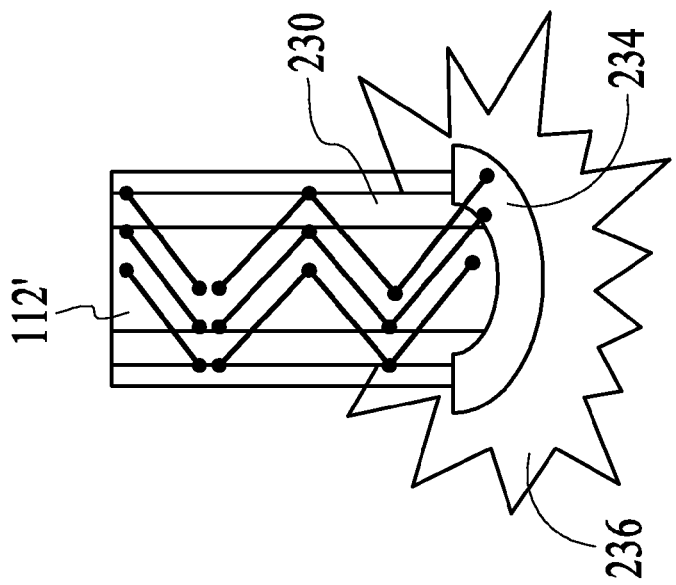

FIG. 8 is a representative detail isometric drawing of an embodiment of the cellulite and adipose tissue treatment system 200 of the present invention. FIG. 9A is a representative detail isometric drawing of an embodiment of the cellulite and adipose tissue treatment system 200′ of the present invention. FIG. 9B is an exploded view of an alternative embodiment of the cellulite and adipose tissue treatment system 200′ of the present invention. FIGS. 10A, 10B and 10C are representative section views of an embodiment of the firing tip 230 best shown in FIGS. 7, 8, 9A and 9B.

As described above with regard to FIG. 7, an embodiment of the front fire fiber optic probe 610′comprises a coated fiber optic laser delivery device 112′. The coated fiber optic 112′ is secured into a Touhy Borst or equivalent clamp 210. A sideport 220 is useful for optional aspiration of liquefied fat, blood or other tissue. As shown, the Touhy Borst clamp adapter 210 is used to fix the length of the fiber 112′ so that the fiber tip 230 of the fiber 112′ is guaranteed to extend beyond the distal tip 224 of the cannula 222. The Touhy Borst adapter 210 essentially clamps to the fiber 112′ to mark proper extension of the fiber tip 230 past the distal end 224 of the cannula 222. The cannula 222 further comprises a tip bushing 226 at the distal end 224 which is made of protective, heat-resistant material including Teflon® and other suitable materials to prevent damage to the fiber tip 230 when fiber tip 230 is extending or protruding out. In one embodiment, fiber tip 230 assists in advancing the cannula 222 by cutting through fibrous strands 122.

As described above, the present invention is a method for treating cellulite and adipose tissue by moving the distal tip 230 of the optical fiber 112′ past the distal end 224 of the cannula 222 so that heat does not impinge on the tip bushing 226 of the end of the cannula 222 and heat it up. In one embodiment, the smooth and blunt end of the cannula 222 prevents inadvertent puncture of skin and is safer overall to use. The apparatus includes a relatively stiff or rigid polyimide coated optical fiber 112′, optionally cleaved flat or at an angle, providing the advantage of not requiring the use of the cannula 222 and resistance by the fiber 112′ to breakage particularly during placement or use. By extending the firing tip 230 of the fiber optic 112′ past the distal end 224 and tip bushing 704 of the cannula 222, the firing tip 230 is well beyond the distal tip 224 of the cannula 222 and there is no risk of overheating the tip 224 or cannula 222.

The cladding 232 of the fiber 112′ is not stripped off prior to use. The fiber 112′ can be cleaved through the entire coating 232. Thus, laser energy heats the coating 232 creating a carbonized tip 234. Thus, the laser energy goes mostly into heating the fiber tip 230 and directly to target tissue 120. In one embodiment, the pulsed hot tip laser explodes the tissue and fat 120 without extensive thermal effects. Fat is liquefied or ablated, and the pulsed laser creates an explosively hot cutting tip 230.

In an embodiment, the fiber coating 232 is made of a material which absorbs the laser energy at the wavelength utilized. During use, it is an advantage to cause the distal end of the coating 232 to burn to a char 234 during laser delivery. The char 234 heats to a very high temperature and acts as a hot tip ablation device, having a hat, ablative cutting surface. In an embodiment of the present invention, the method using a pulsed laser in conjunction with a coated fiber 112′ such that the rapid temperature rise at the charred fiber tip 230 causes an acoustic explosion which ablates and disrupts tissue. The pulsed energy ablates a zone 236 of tissue with minimal peripheral or other unintended thermal damage. Photoacoustic ablation is similar to CW Nd:YAG sapphire crystal contact tip technology. The tip 230 requires an "initiation" to enable the carbon char 234 at the distal end 230 of the coated fiber 112′ to function as a hot cutting tip. The carbon layer 234 on the tip 230 absorbs laser energy, creating an intense white hot ablation point. The system adds short pulse length pulsed energy to achieve a white hot acoustic ablation mechanism. Thus, ablation of connective tissue occurs at low energy fluences, with resultant minimal collateral damage.

The tip 230 of the coated fiber 112′ can be inserted beyond or past the distal tip 224 of the cannula 222 so that it is no longer adjacent the cannula tip 224, increasing maneuverability and improving the efficiency of the cutting tip 230. Additionally, by moving the distal tip 230 of the optical fiber 112′ well past the tip bushing 226 of the cannula 222 there is less chance that the metal cannula 222 will be heated by the laser beam exiting from the emitting face or tip 234 of the fiber 112′, it provides an advantage to minimize heating of the tip 224 of the cannula 222 which if heated may cause burns to the patient's skin as it is introduced and/or withdrawn before, during or after use.

It is also possible to use a Touhy Borst clamp 210 on the fiber 112′ as a marker during other types of visualization including optical, X-ray, sonic imaging, MRI, CAT-scan or other spectral analysis visualization, to guarantee that the fiber 112′ is well beyond the cannula tip 224. Using an aiming beam such as element 137 shown in FIG. 4, up to 10 times or more brighter than the conventional aiming beam, the practitioner can easily determine exactly where the fiber tip 230 is and be able to move it well past the cannula tip 224 before firing it to ablate undesirable connective tissue 122 and melt fat 120.

In one embodiment, the firing tip 230 of the fiber optic 112′ extends beyond and projects out from a blunt distal end 224 of the cannula 222 assisting in advancing the cannula 222 by cutting through fibrous strands 122 as the firing tip 230 advances. The protrusion of firing tip 230 beyond the tip bushing 226 of the blunt distal end 224 of the cannula 222 allows the simultaneous effect of fatty tissue 124 ablation and of heating fatty tissue 124 to cause collagen contraction or collagen stimulation which would not be possible with a fiber end 614 enclosed (not shown) within the end 224 of the cannula 222.

FIG. 9A is a representative detail drawing of an embodiment of the cellulite and adipose tissue treatment system 200′ of the present invention with an alternative embodiment of cannula 222′. FIG. 9B is an exploded view of an alternative embodiment of the cellulite and adipose tissue treatment system 200′ of the present invention. As shown in FIGS. 9A and 9B, there are a plurality of suction holes 702 on one or more sides of the hollow cannula 222′ similar to conventional liposuction handpieces. The main function of suction holes 702 are to provide an opening to allow liquefied fat, blood and other tissues to drain during operation of cellulite and adipose tissue treatment system 200′. In one embodiment, fiber optic 112′ protrudes out the distal end 224 of cannula 222′ by a sufficient distance to not be adjacent. Optionally, fiber optic 112' has a thin coating on it to prevent breakage. The cannula 222' is used to aspirate or suction out tissue 122 or fat 124 that has been melted or ablated by the laser. The suction and aspiration occurs around fiber optic 112' inside the cannula 222'. As shown in FIG. 9B, a Touhy Borst adapter can be used to seal suction off from the suction port 220 on the cannula 222'. In one embodiment, fiber tip 230 will still exit the cannula 222' at the distal end 224 near the tip bushing 226 which internal diameter is in close tolerance to the fiber tip 230 so that suction is not lost from the suction holes 702. In one embodiment, fiber optic 112' can be 100 to 1000 um in diameter and preferably 320 to 600 um. The coating for fiber optic 112' can be Teflon® or other plastic. The coating is preferably a harder coating to allow additional room inside the cannula 112' for aspiration. The hard coating on the fiber optic 112' is preferably polyimide but can also be gold or other hard materials. A thin coating is preferred to allow room inside the cannula 212' for both the fiber optic 112' and the aspirated material to move without clogging up the hollow cannula 222'.

The laser 504 can be any laser, either pulsed or continuos laser, that will ablate or melt tissue 122 or fat 124 and is transmittable through fiber optics 112'. The laser 504 is preferably laser with wavelength of 330 to 3000 nm, or with wavelength of 800 to 2200 nm or with wavelength of 1320 nm. For pulsed laser, it is preferably laser with pulse length of 50-400 micro seconds. As shown in FIG. 7, while fiber tip 230 is advancing, fatty tissue 124 is liquefied and causes increasing popping sound of the pulsed or continuous laser 504. The phenomenon will then trigger suction function of the cannula 222'. In one embodiment, liquefied fat tissue 124, blood and other tissues are sucked through suction holes 702, through the entire cannula 222' and ultimately drained through the side port 220. Aspiration and suction of liquefied fat, blood and other tissues is only activated when the cannula 222' is advancing and liquefied fat, blood and other tissues can be sucked out through the side port 220. In so doing, cannula 222' is being pushed further into the liquefied fat and achieve the optimal and higher laser ablation efficiency.

As best shown in FIG. 5, the treatment system 100 of present invention has a temperature sensor 137 set up in a way that measures the temperature of the skin surface 116 in real time during the treatment pulse sequence and to control the energy source 102 and ultimately the intensity of laser power 504 with a feedback loop so that the skin temperature 506 never reaches damage threshold. However, a non contact sensor 137 can only detect skin surface temperature 506 but not the treated tissue temperature. The disadvantage of this non contact method is that the measurement is not very accurate and largely depends on skin thickness, density and surrounding temperature. As shown in FIG. 9B, there is a thermal sensory device 282 such as a thermocouple placed inside the hollow cannula 222'. As best shown in FIG. 9B, thermal sensory device 282 is located behind the fiber tip 230 such that emitted laser power 504 does not impinge directly on the thermal sensory device 282 and artificially heat it up. In one embodiment, thermal sensory device 282 should only come into contact with treated tissue 120 after tissue has been heated up by the laser 504. Temperature of treated tissue 120 is then detected by thermal sensory device 282 in real time. The other end of thermal sensory device 282 is connected to temperature feedback port 280 to provide temperature feedback which is ultimately looped back to the energy source control system 106.

Fat is very difficult to target using conventional selective photothermolysis. Table 1 shows the optical absorption of laser energy created by an Nd:YAG laser in fat tissue.

Optical absorption of Nd:YAG wavelengths:

TABLE 1

Optical Absorption of Fat

| 1064 | Fat = 0.06 | Tissue = 0.14 |
| 1320 | Fat = 0.16 | Tissue = 1.60 |

The treatment of the present invention does not depend upon optical absorption properties of fat. The pulsed hot tip laser energy explodes tissue and fat without extensive thermal effects. Fat is liquefied, not cooked. Thus, pulsed energy at 1320 nm wavelength ablates very similar to pulsed energy at 1064 nm. Furthermore, 1320 nm also tightens the sub dermal collagen better than energy at 1064 nm.

Table 2 shows a comparison of the collateral tissue damage caused by various types of electromagnetic energy.

TABLE 2

Collateral Tissue Damage

| Device/Wavelength | Power | Depth |
|---|---|---|
| Electrocautery | #4 cut mode | 924 µm |
| Ho:YAG 2.1 µm | 4 Watts | 321 µm |
| CO2 10.6 µm | 3 Watts | 221 µm |
| Nd:YAG 1.06 µm | 3 Watts | 132 µm |
| Nd:YAG 1.32 µm | 3 Watts | 127 µm |
| Nd:YAG 1.32 µm | 4 Watts | 181 µm |

Table 3 shows the effect of pulse width, ablation width and coagulation width.

TABLE 3

Effect of Pulse Width

| Time | Ablation Width | Coagulation Width |
|---|---|---|
| 120 µsec | 987 µm | 49 µm |
| 500 µsec | 593 µm | 63 µm |
| 1200 µsec | 515 µm | 81 µm |

In conclusion, shorter pulses ablate more tissue with less collateral damage to tissue. Energy at 1320 nm used for acoustic ablation shows less collateral damage than electrocautery, $CO_2$, and Holmium lasers in a pulsed cutting mode. This is the opposite action predicted by non-contact thermal and selective photothermolysis theory. Thus, it has been shown that acoustic ablation is a new mechanism to treat tissue with low absorption. According to the present invention described herein, treatment can be made using a variable pulsed laser that can switch between microsecond ablative pulses and millisecond thermal pulses.

Figure 11:
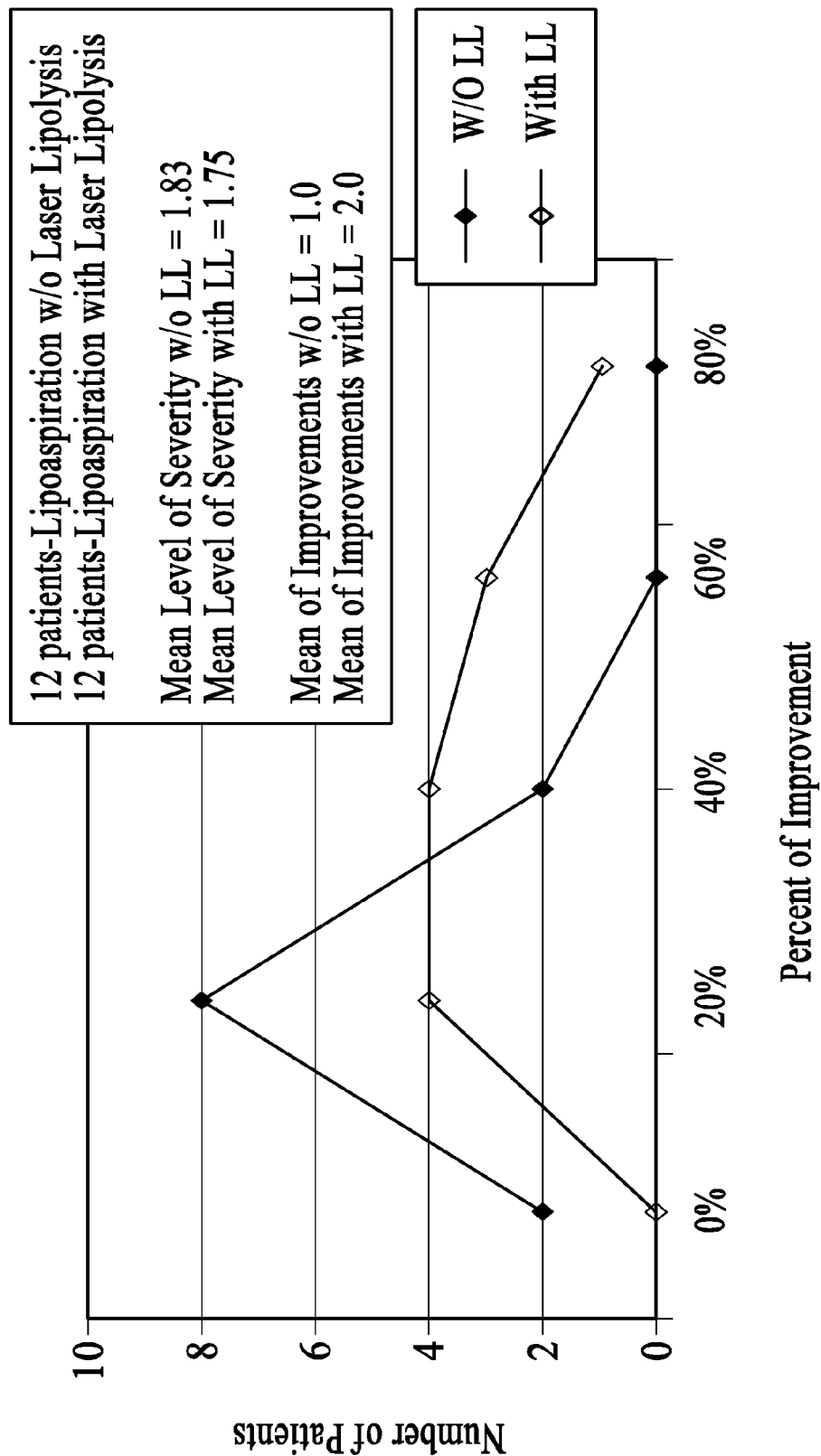
FIG. 11 is a graph showing experimental data obtained from controlled studies of lipoaspiration with and without laser lypolysis.

FIG. 11 is a graph showing experimental data obtained from controlled studies of lipoaspiration with and without laser lypolysis. The data was collected based on experimental results from 12 patients treated using conventional lipoaspiration without laser lipolysis. Data was also collected from an additional 12 patients treated using conventional lipoaspiration with laser lipolysis.

The results showed a mean level of severity of trauma induced by the conventional lipoaspiration treatment without laser lipolysis of 1.83, while the mean level of severity of trauma induced by the conventional lipoaspiration treatment with laser lipolysis was 1.75, or a decrease in over 10%. Furthermore, results showed a mean level of improvement of the patient experienced during healing from the conventional lipoaspiration treatment without laser lipolysis of 1.0, while the mean level of improvement from the conventional lipoaspiration treatment with laser lipolysis was 2.0, or a two-fold increase.

The present invention incorporates U.S. Pat. No. 5,820,626 issued Oct. 13, 1998 to Baumgardner and U.S. Pat. No. 5,976,123 issued Nov. 2, 1999 to Baumgardner et al. herein by reference in their entirety, without limitations, and in particular with regard to their teachings regarding surface cooling of tissue during laser treatment.

Wound Healing and Growth Factors; Mesotherapy and Lipotherapy

When a tissue is injured, polypeptide growth factors, which exhibit an array of biological activities, are released into the wound where they play a crucial role in healing (see, e.g., Hormonal Proteins and Peptides (Li, C. H., ed.) Volume 7, Academic Press, Inc., New York, N.Y. pp. 231 277 (1979) and Brunt et al., Biotechnology 6:25 30 (1988)). These activities include recruiting cells, such as leukocytes and fibroblasts, into the injured area, and inducing cell proliferation and differentiation. Growth factors that may participate in wound healing include, but are not limited to: platelet-derived growth factors (PDGFs); insulin-binding growth factor-1 (IGF-1); insulin-binding growth factor-2 (IGF-2); epidermal growth factor (EGF); transforming growth factor-α (TGF-α); transforming growth factor-β (TGF-.β); platelet factor 4 (PF-4); and heparin binding growth factors one and two (HBGF-1 and HBGF-2, respectively).

PDGFs are stored in the alpha granules of circulating platelets and are released at wound sites during blood clotting (see, e.g., Lynch et al., J. Clin. Invest. 84:640 646 (1989)). PDGFs include: PDGF; platelet derived angiogenesis factor (PDAF); TGF-β; and PF4, which is a chemoattractant for neutrophils (Knighton et al., in Growth Factors and Other Aspects of Wound Healing: Biological and Clinical Implications, Alan R. Liss, Inc., New York, N.Y., pp. 319 329 (1988)). PDGF is a mitogen, chemoattractant and a stimulator of protein synthesis in cells of mesenchymal origin, including fibroblasts and smooth muscle cells. PDGF is also a nonmitogenic chemoattractant for endothelial cells (see, for example, Adelmann-Grill et al., Eur. J. Cell Biol. 51:322 326 (1990)).

IGF-1 acts in combination with PDGF to promote mitogenesis and protein synthesis in mesenchymal cells in culture. Application of either PDGF or IGF-1 alone to skin wounds does not enhance healing, but application of both factors together appears to promote connective tissue and epithelial tissue growth (Lynch et al., Proc. Natl. Acad. Sci. 76:1279 1283 (1987)).

TGF-β is a chemoattractant for macrophages and monocytes. Depending upon the presence or absence of other growth factors, TGF-β may stimulate or inhibit the growth of many cell types.

Other growth factors, such as EGF, TGF-α, the HBGFs and osteogenin are also important in wound healing. Topical application of EGF accelerates the rate of healing of partial thickness wounds in humans (Schultz et al., Science 235:350 352 (1987)). Osteogenin, which has been purified from demineralized bone, appears to promote bone growth (see, e.g., Luyten et al., J. Biol. Chem. 264:13377 (1989)). In addition, platelet-derived wound healing formula, a platelet extract which is in the form of a salve or ointment for topical application, has been described (see, e.g., Knighton et al., Ann. Surg. 204:322 330 (1986)).

The heparin binding growth factors (HBGFs), including the fibroblast growth factors (FGFs), which include acidic HBGF (aHBGF also known as HBFG-1 or FGF-1) and basic HBGF (bHBGF also known as HBGF-2 or FGF-2), are potent mitogens for cells of mesodermal and neuroectodermal lineages, including endothelial cells (see, e.g., Burgess et al., Ann. Rev. Biochem. 58:575 606 (1989)). In addition, HBGF-1 is chemotactic for endothelial cells and astroglial cells. Both HBGF-1 and HBGF-2 bind to heparin, which protects them from proteolytic degradation. The array of biological activities exhibited by the HBGFs suggests that they play an important role in wound healing.

Basic fibroblast growth factor (FGF-2) is a potent stimulator of angiogenesis and the migration and proliferation of fibroblasts (see, for example, Gospodarowicz et al., Mol. Cell. Endocinol. 46:187 204 (1986) and Gospodarowicz et al., Endo. Rev. 8:95 114 (1985)). Acidic fibroblast growth factor (FGF-1) has been shown to be a potent angiogenic factor for endothelial cells (Burgess et al., supra, 1989). Other FGF's may be chemotactic for fibroblasts. Growth factors are, therefore, potentially useful for specifically promoting wound healing and tissue repair.

"HBGF-1," which is also known to those of skill in the art by alternative names, such as endothelial cell growth factor (ECGF) and FGF-1, as used herein, refers to any biologically active form of HBGF-1, including HBGF-1β, which is the precursor of HBGF-1α. and other truncated forms, such as FGF. U.S. Pat. No. 4,868,113 to Jaye et al., herein incorporated by reference, sets forth the amino acid sequences of each form of HBGF. HBGF-1 thus includes any biologically active peptide, including precursors, truncated or other modified forms, or mutants thereof that exhibit the biological activities, or a subset thereof, of HBGF-1.

Two substances commonly used in injections to "dissolve" fat are phosphatidylcholine (PPC) and sodium deoxycholate. The present invention utilizes multiple sessions and many injections of the chemicals. Mesotherapy is a more general term for a variety of minimally invasive techniques in which different medications are directly injected into the skin and the layer beneath the skin for many reasons including musculoskeletal problems, neurological problems and cosmetic conditions. Lipodissolve or lipotherapy, or several other terms, refers specifically to the treatment of fat deposits thru injections.

Other growth factors, mesotherapy and lipotherapy drugs may also be known to those of skill in the art by alternative nomenclature. Accordingly, reference herein to a particular growth factor by one name also includes any other names by which the factor is known to those of skill in the art and also includes any biologically active derivatives or precursors, truncated mutant, or otherwise modified forms thereof.

U.S. Pat. No. 7,094,252 issued Aug. 22, 2006 entitled ENHANCED NONINVASIVE COLLAGEN REMODELING, U.S. Pat. No. 7,217,265 issued May 15, 2007 entitled TREATMENT OF CELLULITE WITH MID-INFRARED RADIATION, and U.S. patent application Ser. No. 11/612,324 filed Dec. 18, 2006 entitled ENDOVENOUS LASER TREATMENT GENERATING REDUCED BLOOD COAGULATION, are all incorporated herein by reference in their entireties.

Unless defined otherwise, all technical and scientific terms used herein have the same meaning as commonly understood by one of ordinary skill in the art to which the present invention belongs. Although any methods and materials similar or equivalent to those described can be used in the practice or testing of the present invention, the methods and materials are now described. All publications and patent documents referenced in the present invention are incorporated herein by reference.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true purview, spirit and scope of the invention.

We claim:

1. A method for laser-assisted liposuction, the method comprising the steps of:
    providing a hollow cannula with a blunt, non-piercing distal tip, an integral suction system, and an optical fiber located inside or adjacent to the cannula and extending through or along the cannula, the optical fiber having an emitting tip extending beyond the blunt, non-piercing distal tip of the cannula, and the optical fiber having a proximal end for connecting to a laser source;
    providing the laser source, the laser source having emitting characteristics for generating a laser beam transmittable through the optical fiber, the laser beam having an intensity and a wavelength capable of melting or disrupting cellulite and adipose tissue;
    generating the laser beam with the laser source and delivering laser energy from the emitting tip of the optical fiber to the tissue;
    placing the blunt, non-piercing distal tip of the cannula underneath the dermis of a patient;
    moving the emitting tip of the optical fiber beyond the blunt, non-piercing distal tip of the cannula into the cellulite and adipose tissue of the patient;
    irradiating the cellulite and adipose tissue with the laser beam to melt or disrupt the cellulite and adipose tissue prior to the cellulite and adipose tissue entering the cannula without heating the blunt, non-piercing distal tip of the cannula;
    acoustically determining a presence of melted fat prior to activation of suction for removal of aspirate; and
    activating the suction system to remove and aspirate melted fat and ablated tissue particles.

2. The method of claim 1 in which an increase in popping sounds determine the presence of melted fat prior to activation of suction for removal of aspirate.

3. The method of claim 1 further comprising the following step:
    delivering wound healing compounds, lipotherapy and/or meseotherapy drugs through the hollow cannula to the laser treated cellulite or adipose tissue.

4. The method according to claim 1, further comprising determining a presence of melted fat by an increase in popping sounds prior to activation of suction from removal of aspirate.

5. The method according to claim 1, further comprising cutting through fibrous strands of connective tissue in the cellulite and adipose tissue with the emitting tip of the optical fiber while the cannula is advancing through the connective structure, cellulite, and adipose tissue.

6. The method according to claim 1, further comprising placing the emitting tip of the optical fiber in direct contact with the tissue to provide increased power density and faster ablation of the tissue.

7. The method according to claim 1, further comprising collection real-time thermal feedback from a thermal sensor located at a site of the cellulite and adipose tissue being treated.

8. The method according to claim 7, further comprising monitoring a thermal profile of the tissue to prevent undesirable damage to the tissue.

9. The method according to claim 7, further comprising controlling an intensity of the laser beam to prevent undesirable damage to the tissue.

10. A method for laser-assisted liposuction, the method comprising the steps of:
    providing a hollow cannula with a blunt, non-piercing distal tip, an integral suction system, and an optical fiber located inside or adjacent to the cannula and extending through or along the cannula, the optical fiber having an emitting tip extending beyond the blunt, non-piercing distal tip of the cannula, the optical fiber having a proximal end for connecting to a laser source;
    providing a laser source with emitting characteristics for generating a laser beam transmittable through the optical fiber, the laser beam having an intensity and a wavelength capable of melting or disrupting cellulite and adipose tissue;
    generating the laser beam with the laser source and delivering laser energy from the emitting tip of the optical fiber;
    placing the blunt, non-piercing distal tip of the cannula underneath the dermis of a patient;
    moving the emitting tip of the optical fiber beyond the blunt, non-piercing distal tip of the cannula into the cellulite and adipose tissue of the patient;
    irradiating the cellulite and adipose tissue with the laser beam to melt or disrupt the cellulite and adipose tissue prior to the cellulite and adipose tissue entering the cannula without heating the blunt, non-piercing distal tip of the cannula,
    determining a presence of melted fat by an increase in popping sounds prior to activation of suction for removal of aspirate; and
    activating the suction system to remove and aspirate melted fat and ablated tissue particles.

11. The method of claim 10 further comprising the following step:
    delivering wound healing compounds, lipotherapy and/or meseotherapy drugs through the hollow cannula to the laser treated cellulite or adipose tissue.

12. The method according to claim 10, further comprising acoustically determining a presence of melted fat prior to activation of suction for removal of aspirate.

13. The method according to claim 10, further comprising cutting through fibrous strands of connective tissue in the cellulite and adipose tissue with the emitting tip of the optical fiber while the cannula is advancing through the connective structure, cellulite, and adipose tissue.

14. The method according to claim 10, further comprising placing the emitting tip of the optical fiber in direct contact with the tissue to provide increased power density and faster ablation of the tissue.

15. The method according to claim 10, further comprising collection real-time thermal feedback from a thermal sensor located at a site of the cellulite and adipose tissue being treated.

16. The method according to claim 15, further comprising monitoring a thermal profile of the tissue to prevent undesirable damage to the tissue.

17. The method according to claim 15, further comprising controlling an intensity of the laser beam to prevent undesirable damage to the tissue.

* * * * *